(12) United States Patent
Gerrans et al.

(10) Patent No.: US 9,694,075 B2
(45) Date of Patent: *Jul. 4, 2017

(54) TREATMENT OF HYPOXIC TUMORS WITH LOCALIZED OXYGENATION

(75) Inventors: Lawrence J. Gerrans, San Anselmo, CA (US); Erhan H. Gunday, Great Neck, NY (US)

(73) Assignee: Sanovas, Inc., Sausalito, CA (US)

( * ) Notice: Subject to any disclaimer, the term of this patent is extended or adjusted under 35 U.S.C. 154(b) by 1201 days.

This patent is subject to a terminal disclaimer.

(21) Appl. No.: 13/440,695

(22) Filed: Apr. 5, 2012

(65) Prior Publication Data

US 2012/0259152 A1    Oct. 11, 2012

Related U.S. Application Data

(60) Provisional application No. 61/473,481, filed on Apr. 8, 2011.

(51) Int. Cl.
*A61N 5/10* (2006.01)
*A61K 41/00* (2006.01)
*A61K 45/06* (2006.01)
*A61K 31/704* (2006.01)
*A61K 31/195* (2006.01)
(Continued)

(52) U.S. Cl.
CPC .......... *A61K 41/008* (2013.01); *A61K 9/1647* (2013.01); *A61K 31/195* (2013.01); *A61K 31/704* (2013.01); *A61K 33/00* (2013.01); *A61K 41/00* (2013.01); *A61K 41/0038* (2013.01);
(Continued)

(58) Field of Classification Search
CPC ................ A61K 41/00; A61K 41/0004; A61K 41/0038; A61K 41/0057; A61K 41/008; A61N 5/10; A61N 5/1001; A61N 5/1002; A61N 5/1007; A61N 5/1014; A61N 2005/1098; A61B 17/22012;
(Continued)

(56) References Cited

U.S. PATENT DOCUMENTS 4,824,436 A    4/1989   Wolinsky
4,979,935 A *  12/1990  Lindmayer ............... 600/2
(Continued)

FOREIGN PATENT DOCUMENTS

JP    2005046419    *  2/2005   ............ A61M 25/00
JP    2005046419 A     2/2005

OTHER PUBLICATIONS

Attached Machine translation of reference.*
(Continued)

*Primary Examiner* — Charles A Marmor, II
*Assistant Examiner* — Carrie R Dorna
(74) *Attorney, Agent, or Firm* — St. Onge Steward Johnston & Reens LLC

(57) ABSTRACT

Methods and systems for treatment of hypoxic tumors are provided, including the steps of positioning a delivery device in a bodily cavity adjacent to tumor tissue, delivering an oxygenating agent to the tumor tissue via the delivery device and radiating the tumor tissue with radiation. Methods and systems of treatment of tumors are also provided, including the steps of positioning a delivery device in a bodily cavity adjacent to tumor tissue, delivering a photosensitizing agent to the tumor tissue via the delivery device, and radiating the tumor tissue with light.

29 Claims, 12 Drawing Sheets

(51) Int. Cl.
  *A61K 33/00* (2006.01)
  *A61K 9/16* (2006.01)
(52) U.S. Cl.
  CPC ............... *A61K 45/06* (2013.01); *A61N 5/10* (2013.01); *A61N 2005/1098* (2013.01)
(58) Field of Classification Search
  CPC ..... A61B 17/32075; A61B 17/320725; A61M 2025/109
  See application file for complete search history.

(56) References Cited

U.S. PATENT DOCUMENTS

| | | | |
|---|---|---|---|
| 5,823,993 A | 10/1998 | Lemelson | |
| 5,843,089 A * | 12/1998 | Sahatjian | A61F 2/958 128/898 |
| 6,159,686 A | 12/2000 | Kardos et al. | |
| 6,575,932 B1 | 6/2003 | O'Brien et al. | |
| 6,685,718 B1 * | 2/2004 | Wyzgala | A61B 17/320725 606/170 |
| 6,716,426 B1 | 4/2004 | Maeda et al. | |
| 7,338,670 B2 | 3/2008 | Dewhirst et al. | |
| 2003/0208249 A1 | 11/2003 | Chen | |
| 2005/0112131 A1 * | 5/2005 | Pogue et al. | 424/178.1 |
| 2005/0222116 A1 * | 10/2005 | Tsuchida et al. | 514/185 |
| 2008/0171985 A1 | 7/2008 | Karakoca | |
| 2009/0024087 A1 | 1/2009 | Kennedy, II et al. | |
| 2009/0326508 A1 * | 12/2009 | Braun | A61M 25/0009 604/500 |
| 2010/0121270 A1 | 5/2010 | Gunday et al. | |
| 2011/0152683 A1 | 6/2011 | Gerrans et al. | |
| 2011/0218494 A1 | 9/2011 | Gerrans et al. | |
| 2011/0270126 A1 | 11/2011 | Gunday et al. | |
| 2011/0270184 A1 | 11/2011 | Gunday et al. | |

OTHER PUBLICATIONS

Celikoglu, et al.; "Bronchoscopic Intratumoral Chemotherapy of Lung Cancer"; Lung Cancer; Jul. 2008; 1 page abstract.
Jiang, et al.; "Doxorubicin-Gallium-Transferrin and Cisplatin-Transferrin Conjugated Reverse Hypoxia-Induced Drug Resistance in Breast Cancer MCF-7 Cells"; Proc Amer Assoc Cancer Res, vol. 45; 2004; 1 page abstract.
Isa, et al; "Hypoxia in Head and Neck Cancer"; The British Journal of Radiology, Oct. 2006; pp. 791-798.
Goldberg, et al; "Intratumoral Cancer Chemotherapy and Immunotherapy: Opportunities for Nonsystemic Preoperative Drug Delivery"; J. Pharm Pharmacol.; Feb. 2002; 1 page (abstract from PubMed).
Cairns, et al.; "Metabolic Targeting of Hypoxia and HIF1 in Solid Tumors can Enhance Cytotoxic Chemotherapy"; Division of Radiation and Cancer Biology, Department of Radiation Oncology, Stanford University School of Medicine; Published Apr. 2007; retrieved via internet link: http://www.pnas.org/content/104/22/945.full on Jan. 3, 2011; 14 pages.
Verma, et al.; "Photodynamic Tumor Therapy: Mitochondrial Benzodiazepine Receptors as a Therapeutic Target"; Molecular Medicine; 4: pp. 40-45; 1998.
Brown, et al.; "Reversing Hypoxic Cell Chemoresistance in Vitro Using Genetic and Small Molecule Approaches Targeting Hypoxia Inducible Factor-1"; Molecular Pharmacology; 2006; pp. 411-418.
Wouters, et al.; "Review: Implications of In Vitro Research on the Effect of Radiotherapy and Chemotherapy Under Hypoxic Conditions"; Oncologist 2007; 12; 690-712.
Eun-Jin Yeo, et al; "YC-1: A Potential Anticancer Drug Targeting Hypoxia-Inducible Factor 1"; Journal of the National Cancer Institute, vol. 95, No. 7, Apr. 2, 2003; pp. 516-525.
Dean et al., "Fibrinolytic Inhibitors for Cancer-Associated Bleeding Problems", Journal of Pain and Symptom Management, vol. 13 No. 1, Jan. 1997.
Lin Feng et al. 2008. In vivo and in situ cellular image processing and characterization: challenges and solutions. In Proceedings of the 7th WSEAS International Conference (IMACS'08), Qing Li, S. Y. Chen, Anping Xu, and Ming Li (Eds.). World Scientific and Engineering Academy and Society (WSEAS), Stevens Point, Wisconsin, USA, 157-162.
Rajput and Agrawal, "Microspheres in cancer therapy", Indian Journal of Cancer, Oct.-Dec. 2010, vol. 47, Issue 4.
Papadopoulou et al., "Novel Non-invasive Probes for Measuring Tumor-hypoxia by 19F-Magnetic Resonance Spectroscopy (19F-MRS). Studies in the SCCVII/C3H Murine model", Anticancer Research 26:3259-3264 (2006).

* cited by examiner

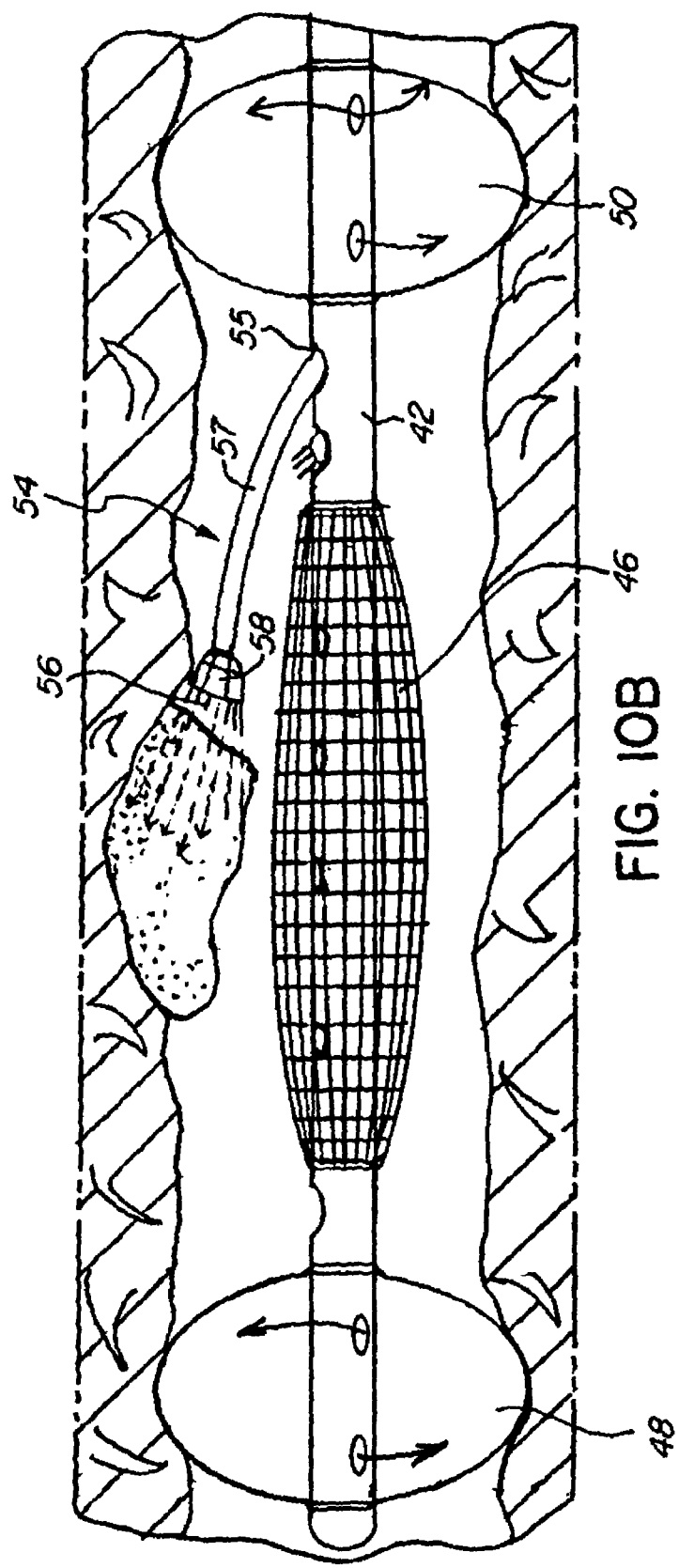
FIG. IOB

TREATMENT OF HYPOXIC TUMORS WITH LOCALIZED OXYGENATION

CROSS-REFERENCE TO RELATED APPLICATIONS

The present application claims the benefit under 35 U.S.C. §119(e) of the U.S. Provisional Patent Application Ser. No. 61/473,481 filed on Apr. 8, 2011, the content of which is incorporated by reference herein in its entirety.

FIELD OF THE INVENTION

The present invention relates to methods of treatment of cancerous tumors. More specifically, the invention relates to a method of treatment of hypoxic malignant tumors with localized oxygenation and synchronized radiation treatment.

BACKGROUND OF THE INVENTION

Radiation therapy, also known as radiation oncology, is the general term for any treatment involving medical use of ionizing radiation to destroy malignant cells. Radiation therapy affects malignant tissue cells by damaging cells' DNA by either a direct or indirect ionization of the atoms that make up the DNA chain.

Indirect ionization refers to the ionization of water, which leads to the formation of free hydroxyl radicals that damage the DNA. This type of ionization is typically achieved by the use of photon energy. Direct ionization occurs via direct energy transfer from the charged particles, such as proton, boron, carbon or neon ions, to the cancerous cells, thereby causing breaks in the cells' double-stranded DNA.

One of the most common problems encountered during the radiation therapy of malignant tumors is that the tumor cells become deficient in oxygen—a condition referred to as hypoxia. Hypoxia commonly develops within solid tumors because tumor cell growth is greater than the rate of blood vessel formation. Thus, the increase in tumor mass results in inadequate vasculature formation, which compromises the blood supply. The exposure of tumor cells to a hypoxic environment is associated with angiogenesis, metastasis, radiation resistance, and drug resistance.

It is presently known that oxygen deficiency influences some major intracellular pathways, such as those involved in cell proliferation, cell cycle progression, apoptosis, cell adhesion, and others. When investigating the effects of radiotherapy or chemotherapy under hypoxic conditions, it is essential to consider the influences of hypoxia itself on the cell.

Chronic hypoxia, also referred to as "diffusion-limited" hypoxia, typically occurs in the areas of large intervascular distances that are beyond the diffusion limit of oxygen (i.e., approximately >150 μm). However, the origins of the chronic hypoxia are more complex. Compared with normal tissue vessels, the tumor microvasculature commonly shows characteristic structural and functional abnormalities. Tumor blood vessels display a highly irregular vascular geometry with arteriovenous shunts, blind ends, lack of smooth muscle or enervation, and incomplete endothelial linings. Additionally, the abundant proliferation of tumor cells results in a disturbed balance between oxygen supply and demand. Furthermore, a relative lack of arteriolar input into tumors creates severe longitudinal oxygen partial pressure ($pO_2$) gradients within the vessels themselves. All of these features contribute to the fact that a great portion of tumor cells are situated in chronically hypoxic regions.

An acute hypoxia, or so-called "perfusion-limited" hypoxia, is typically caused by spontaneous fluctuations in tumor blood flow, which produce temporary regions of acute hypoxia. These fluctuations result from transient occlusion and narrowing of vessels and arteriolar vasomotion.

One important issue to consider in any anticancer therapy is in what proportions both types of hypoxia, acute and chronic, are present in human tumors. In the past, chronic hypoxia has always been considered as the most important factor. However, studies have now demonstrated that microregional fluctuations in erythrocyte flow, consistent with transient, perfusion-driven changes in oxygenation, which are the signs of acute hypoxia, are also a common feature of human malignancies. Therefore, it has to be taken into account that both types of hypoxia occur commonly in human tumors.

Oxygen is an essential radiosensitizer during the radiation therapy. The presence of oxygen at the time of irradiation increases the effectiveness of a given dose of radiation by forming DNA-damaging free radicals. During the radiation therapy, a direct ionization or reaction of the radiation with hydroxyl radicals produced by radiolysis of nearby water molecules result in a formation of DNA radicals. Oxygen, which has a very high electron affinity, reacts extremely fast with the free electrons of these radicals, thereby fixing the free radical damage. However, in the absence of oxygen, reducing compounds interact with the DNA radicals by hydrogen donation. This interaction leads to restitution of the DNA to its undamaged state. As a result, hypoxia severely compromises ionizing radiation in its ability to kill malignant cells.

The radio-resistance of hypoxic cells is a serious limitation in attempts to increase the therapeutic ratio between tumor and normal tissue damage in radiotherapy. This disadvantage of hypoxic cells is somewhat reduced in tumors which can reoxygenate their hypoxic cells during fractionated radiotherapy, for example, by shrinkage.

Much research has been devoted to overcoming hypoxia in conjunction with anticancer therapies. Presently known methods of overcoming hypoxia include the use of high pressure oxygen tanks, blood substitutes that carry increased oxygen, radiosensitizing drugs, such as misonidazole and metronidazole, and hypoxic cytotoxins, such as tirapazamine. However, these known methods suffer from a number of significant drawbacks.

One of the major drawbacks of the prior art methods of reversing hypoxia is that the radiosensitizing drugs are typically delivered intravenously. This causes overoxygenation of various bodily tissues which can lead to serious organ damage and even organ failure. For example, doxorubicin, which is commonly used in the treatment of a wide range of cancers and is typically administered intravenously in the form of hydrochloride salt, is highly cardiotoxic, meaning that it causes oversaturation of oxygen in the heart tissue, leading to heart attacks.

Another major drawback of the known methods of overcoming hypoxia is that it usually takes a significant amount of time for the oxygenating agent to reach and absorb into target tumor tissue. This makes it difficult to determine the optimal time for exposing the tumor tissue to radiation to ensure an effective radiotherapy treatment.

Photodynamic therapy has been found effective at treating tumors locally. An especially effective method of photodynamic therapy has been in combination with the use of photosensitizing drugs. However, photodynamic therapy when used, exclusively, and when used in combination with photosensitizing drugs has been found to produce only superficial penetration into the tumor and/or target tissue. Consequently, photodynamic therapy has not been found to be a reliable, long-term curative solution.

Hence, there is a significant need for a method of treatment of hypoxic malignant tumors that is capable of delivering an oxygenating agent directly to tumor tissue in a bodily cavity to ensure more precise and efficient oxygenation of the target tumor site and to avoid exposing surrounding healthy tissue to potentially damaging chemical agents. There is also a need for a method of treatment of hypoxic tumors that allows for a synchronized oxygenation and radiation of tumor tissues to provide a highly effective anticancer therapy. It is also desired to provide a method of treatment of hypoxic tumors that combines radiation and photodynamic therapies. There is further a need to provide a method for treatment of hypoxic tumors wherein absorption of an oxygenating agent can be observed and monitored to ensure the optimal oxygen saturation in tumor tissue.

SUMMARY OF THE INVENTION

Accordingly, it is an object of the present invention to provide a method for treatment of hypoxic tumors that allows for localized delivery of oxygenating agents to tumor tissues in bodily cavities.

It is an object of the present invention to provide a method for resecting the superficial and interstitial tissues using photodynamic therapy and/or photodynamic therapy in concert with locally delivered photosensitizing agents to permit improved uptake of hypoxia reversing drugs and/or cytotoxic agents into the deepest regions of tumors and/or target tissues to facilitate radiation sensitization of those tissues to better enable radiation therapy.

It is also an object of the present invention to provide a method for treatment of hypoxic tumors that allows for synchronized delivery of oxygenating agents to tumor tissues and radiation of the tissues.

It is a further object of the present invention to provide a method for treatment of hypoxic tumors that combines radiation, light emitting and photodynamic therapies to damage and destroy tumor cells.

It is yet a further object of the present invention to provide a method for treatment of hypoxic tumors that allows monitoring of the absorption of an oxygenating agent into tumor tissue.

In order to overcome the deficiencies of the prior art and to achieve at least some of the objects and advantages listed, the invention comprises a method for treatment of hypoxic tumors comprising the steps of positioning a delivery device in a bodily cavity adjacent to tumor tissue, delivering an oxygenating agent to the tumor tissue via the delivery device, and radiating the tumor tissue with radiation.

In some embodiments, the steps of delivering the oxygenating agent to the tumor tissue and radiating the tumor tissue with radiation are synchronized.

In certain advantageous embodiments, the oxygenating agent comprises oxygen. In other advantageous embodiment, the oxygenating agent comprises an oxygenating therapeutic agent. In some of these embodiments, the oxygenating therapeutic agent comprises doxorubicin.

In certain embodiments, the radiation comprises ionizing radiation. In other embodiments, the radiation comprises light, and the method further comprises the step of delivering a photosensitizing agent to the tumor tissue via the delivery device. In some of these embodiments, the photosensitizing agent is an up-converting phosphor.

In some advantageous embodiments, the radiation comprises light and ionizing radiation, and the oxygenating agent comprises a photosensitizing agent.

In certain embodiments, the oxygenating agent comprises a biomarker, and the method further comprises the step of monitoring absorption of the oxygenating agent into the tumor tissue via the biomarker. In some of these embodiments, the biomarker is a radiopaque marker. In certain of these embodiments, the biomarker is a fluorinated compound.

In some advantageous embodiment, the delivery device comprises at least one inflatable balloon and a catheter having a first lumen through which fluid is supplied to the at least one balloon to inflate the balloon and a second lumen for supplying the oxygenating agent to the tumor tissue via at least one opening in the catheter.

In other advantageous embodiments, the step of delivering an oxygenating agent to the tumor tissue comprises injecting the oxygenating agent into the tumor tissue. In some of these embodiments, the delivery device is a delivery probe comprising a housing, at least one delivery capsule for accommodating the oxygenating agent to be delivered movably arranged in the housing, an actuation mechanism for moving the at least one capsule between an activated position and an inactivated position by providing at least one of a fluid and a vacuum, at least one injection device in fluid communication with the at least one capsule, and a delivery mechanism for forcing the oxygenating agent out of the at least one capsule via the at least one injection device.

In certain embodiments, the method further includes the step of measuring partial pressure of oxygen in the tumor tissue prior to delivering the oxygenating agent. In some of these embodiments, the step of measuring partial pressure of oxygen includes determining partial pressure of oxygen in the bodily cavity via a probe inserted into the bodily cavity.

In some advantageous embodiments, the step of measuring partial pressure of oxygen includes extracting at least a portion of the tumor tissue with forceps and determining partial pressure of oxygen in the extracted tissue outside of the bodily cavity. In some of these embodiments, the forceps include a catheter, a sampling chamber positioned at a distal end of the catheter and having a movable cover, and an actuation mechanism for moving the movable cover between a closed position and an opened position by providing at least one of a fluid and a vacuum.

In other advantageous embodiments, the step of measuring partial pressure of oxygen includes extracting at least a portion of the tumor tissue with a resector balloon system and determining partial pressure of oxygen in the extracted tissue outside of the bodily cavity. In certain of these embodiments, the resector balloon system includes a catheter and at least one balloon having an outer wall, the outer wall comprising a resecting surface for resecting the tumor tissue.

In some embodiments, the step of radiating the tumor tissue with radiation includes radiating the tumor tissue from an external source positioned outside of a patient's body. In other embodiments, the step of radiating the tumor tissue with radiation comprises radiating the tumor tissue locally by positioning a source of radiation in the bodily cavity adjacent to the tumor tissue. In some of these embodiments, the source of radiation positioned in the bodily cavity comprises a probe for radiating the tumor tissue. In some cases, the probe delivers a beam of electron radiation to the tumor tissue.

In certain embodiments, the method further includes the step of delivering a vaso-occlusive agent to the tumor tissue.

In some embodiments the vaso-occlusive agent could be in the form of a bio-degradeable, antifibrinolytic drug eluting nanoparticle, such as a tranexamic acid eluting PLGA (D,L-lactide-co-glycolide) microsphere, delivered via direct placement, injection or via the extravasation method.

In some advantageous embodiments, the method includes the steps of resecting the radiated tumor tissue, and repeating the steps of radiating the tumor tissue and resecting the tumor tissue.

A system for the treatment of hypoxic tumors is also provided, comprising a vessel having an oxygenating agent therein, a delivery device for communicating the oxygenating agent from the vessel to tumor tissue, and a radiation source for radiating the tumor tissue after the delivery device has delivered the oxygenating agent to the tumor tissue.

In certain advantageous embodiments the vessel includes a drug eluting nanoparticle, such as a doxorubicin eluting PLGA (D,L-lactide-co-glycolide) microsphere, delivered via direct placement, injection or via the extravasation method.

In some embodiments, the oxygenating agent comprises oxygen. In other embodiments, the oxygenating agent comprises an oxygenating therapeutic agent. In some cases, the oxygenating therapeutic agent comprises doxorubicin.

In some embodiments, the delivery device comprises at least one inflatable balloon and a catheter having a first lumen through which fluid is supplied to the at least one balloon to inflate the balloon and a second lumen for supplying the oxygenating agent to tumor tissue via at least one opening in the catheter.

In certain embodiments, the delivery device comprises a delivery probe including a housing, the vessel comprises a delivery capsule for accommodating the oxygenating agent to be delivered movably arranged in the housing, the delivery probe includes an actuation mechanism for moving the capsule between an activated position and an inactivated position by providing at least one of a fluid and a vacuum, the delivery probe includes at least one injection device in fluid communication with the capsule, and the delivery probe includes a delivery mechanism for forcing the oxygenating agent out of the capsule via the at least one injection device.

Other objects of the invention and its particular features and advantages will become more apparent from consideration of the following drawings and accompanying detailed description.

BRIEF DESCRIPTION OF THE DRAWINGS

FIGS. 10A-C are partially cross-sectional views of the balloon catheter of FIG. 2 used in accordance with the present invention.

DETAILED DESCRIPTION OF THE INVENTION

The present invention provides improved methods of treatment of hypoxic malignant tumors with localized oxygenation and synchronized radiation treatment. The methods comprise the steps of positioning a delivery device in a bodily cavity adjacent to tumor tissue, delivering an oxygenating agent and/or a photosensitizing agent to the tumor tissue via the delivery device, and radiating the tumor tissue with radiation and/or light.

Figure 1:
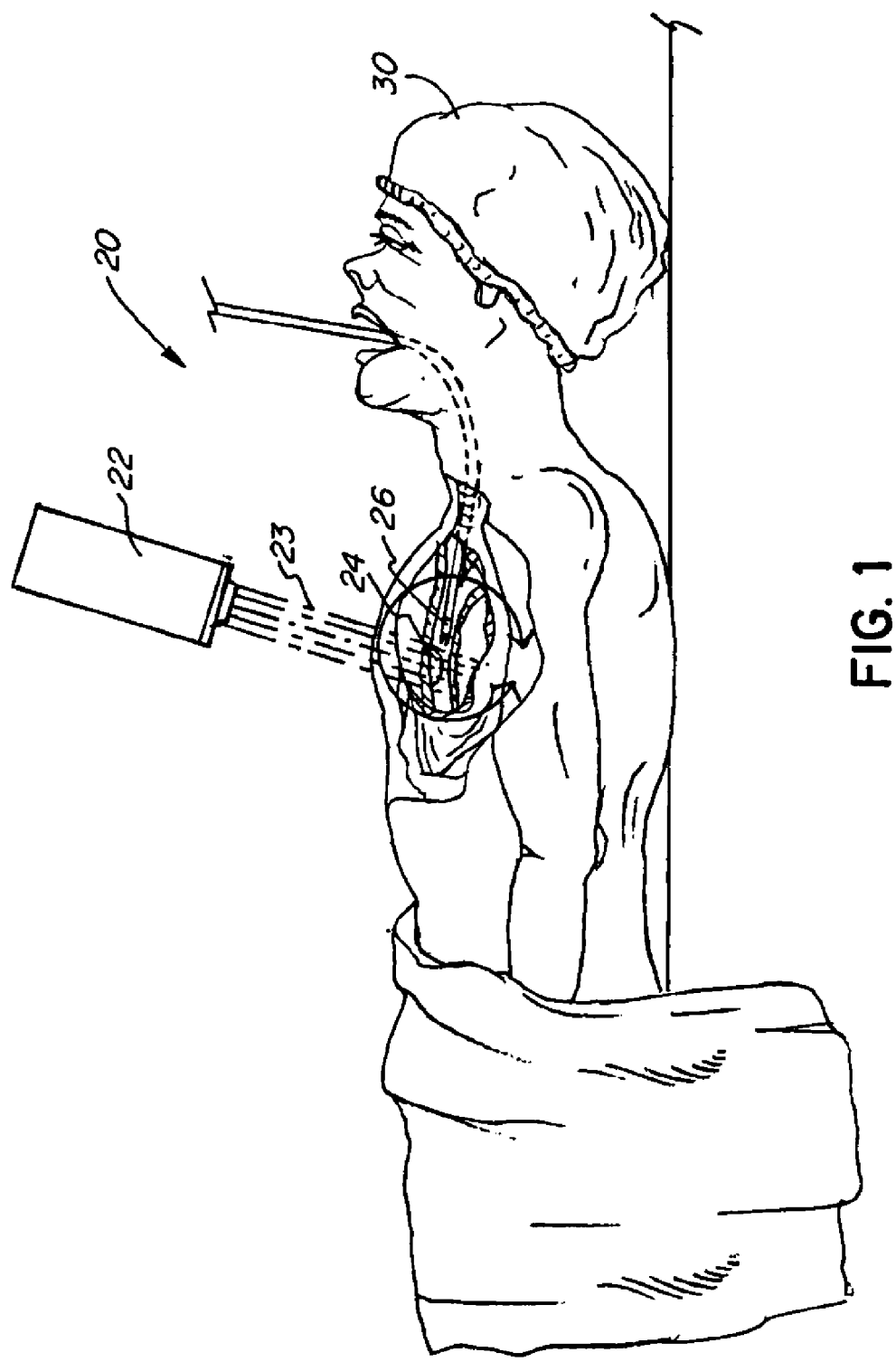
FIG. 1 is a partially exposed side view of a system for treatment of hypoxic tumors according to the present invention in a patient's body.

The basic components of a treatment system useful in the methods of the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system (20) includes a radiation source (22) for radiating tumor tissue (24) inside a patient's (30) bodily cavity, such as a lung. The system (22) further includes a delivery device (26) inserted into the bodily cavity and positioned adjacent to tumor tissue (24). The delivery device (26) is inserted through a natural orifice or through an incision in the patient's body via any suitable type of a catheter (28) and is used to deliver oxygenating and/or photosensitizing agents directly to tumor tissue (24).

Any suitable delivery (26) device may be used in accordance with the present invention. In one preferred embodiment shown in FIG. 2, the delivery device is a balloon catheter system (40), such as that disclosed in U.S. Patent Publication No. 2011-0218494 by Gerrans et al., the disclosure of which is incorporated by reference herein in its entirety. The balloon catheter system (40) includes a catheter (42) and a plurality of inflatable balloons positioned at a distal end (44) of the catheter. In the embodiment shown in FIG. 2, the balloon catheter (42) includes a first balloon (48), a second balloon (50) and a third balloon (46), positioned between the first and second balloons (48, 50). The balloons (46, 48, 50) may be made of latex, Yulex, polyethylene, nylon or other suitable material, and may come in a variety of sizes and diameters, which allow the balloon catheter system (42) to be used in bodily cavities of various diameters and dimensions, such as large and small bronchial branches, sinuses, and blood vessels, having different types of tumors to be treated.

Figure 3:
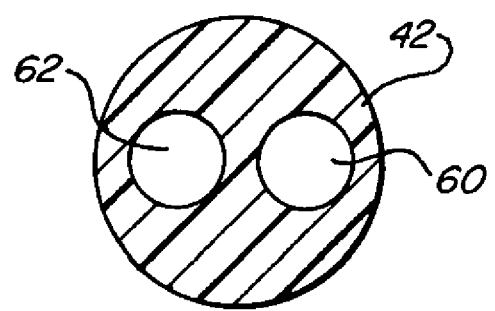
FIG. 3 is a cross-sectional view of a catheter of the system of FIG. 1.

As shown in FIG. 3, the catheter (42) preferably has a first lumen (60) through which fluid is supplied to the balloons (46, 48, 50) via a fluid source to inflate the balloons. The catheter (42) also includes a second lumen (62) for supplying an oxygenating agent and/or photosensitizing agent to tumor tissue (24) via at least one opening (52) in the catheter (42). It is understood that additional lumens can also be provided in the catheter (42) to deliver any number of things to assist insertion and positioning of the balloon catheter system (40) within the bodily cavity and to carry out various diagnostic or therapeutic procedures.

Any suitable fluid source, such as a manually actuated inflation apparatus or an electro-pneumatic pump, may be used in accordance with the present invention. In an advantageous embodiment, the fluid source is an electro-pneumatic pump having controls on the front thereof, from which a physician or assistant can control the system (as well as a remote control unit), such as that disclosed in U.S. Patent Application No. 2010/0121270 by Gunday et al., the specification of which is hereby incorporated by reference herein in its entirety.

Figure 2:
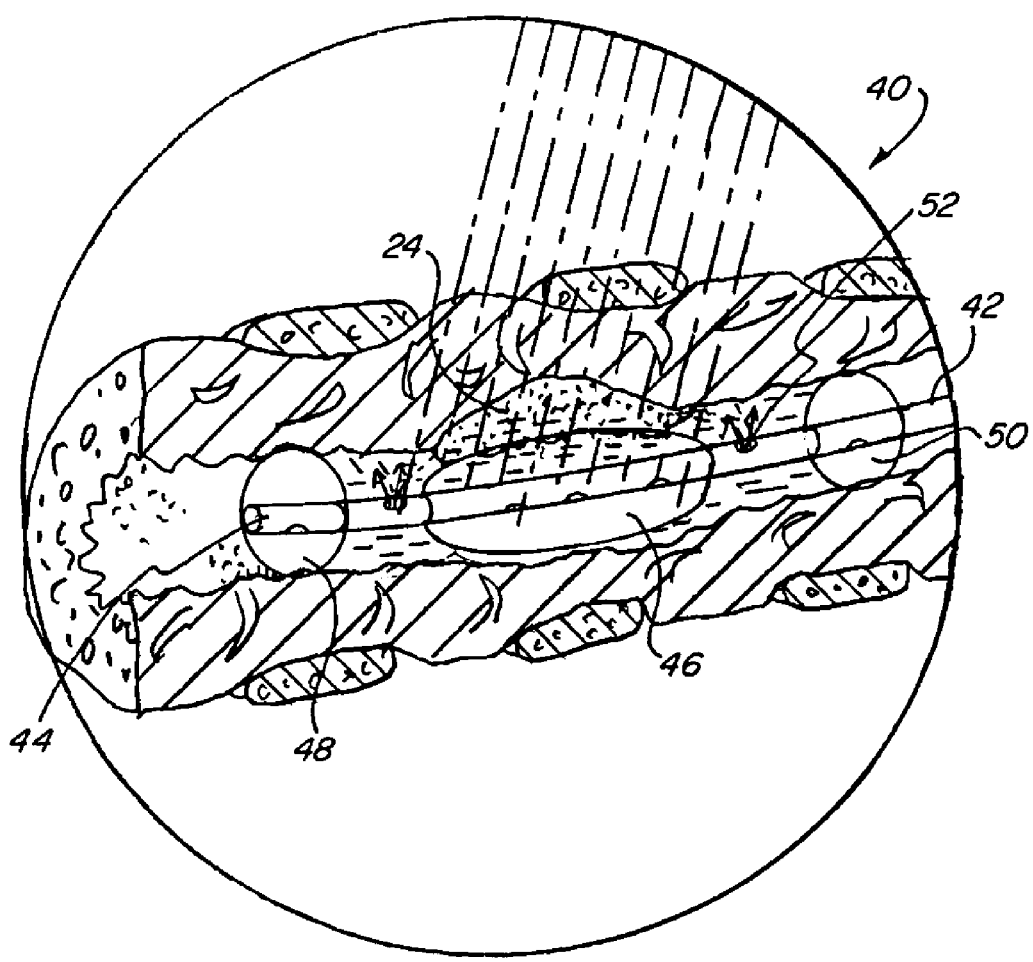
FIG. 2 is an enlarged view of a delivery device of the system of FIG. 1, positioned in a bodily lumen.

In the embodiment shown in FIG. 2, the agent is supplied via one or more openings in the catheter, such as, for example, two openings (52), one positioned between the first balloon (48) and the third balloon (46), and the other positioned between the second balloon (50) and the third balloon (46). It is understood, however, that one opening is sufficient to supply the agent. Additionally, the catheter (42) can include multiple openings positioned at different locations along the catheter (42) to deliver the agent to different locations inside the bodily cavity. Further, an outer wall of the balloons (46, 48, 50) can be provided with openings therein, and the agents can be delivered to tumor tissue through the openings in the balloon walls.

In a preferred embodiment, the catheter (42) includes an imaging device (not shown) disposed in one of the lumens of the catheter (42). The imaging device is used to help position the balloon catheter system at the proper location adjacent to tumor tissue (24). The imaging device can be any device suitable for viewing the target area, such as a coherent fiber bundle or appropriate optical element and lens assembly in conjunction with an imaging sensor (e.g., CMOS, CCD), having a sufficiently small outer diameter. The imaging device can extend out of the openings in the catheter (42) to view the surrounding tissue during the insertion of the catheter into the bodily cavity. Further details regarding the structure and operation of the imaging device are disclosed in U.S. Patent Publication No. 2011-0218494 by Gerrans et al.

It should be noted that other types of balloon catheter systems may be used in accordance with the present invention. For example, the balloon catheter systems disclosed in U.S. Patent Publication No. 2010-0121270 by Gunday et al., U.S. Patent Publication No. 2011-0152683 by Gerrans et al., and 13/037,856 by Gerrans et al. can also be used. The disclosure of each of the above applications is incorporated by reference herein in its entirety.

Figure 4:
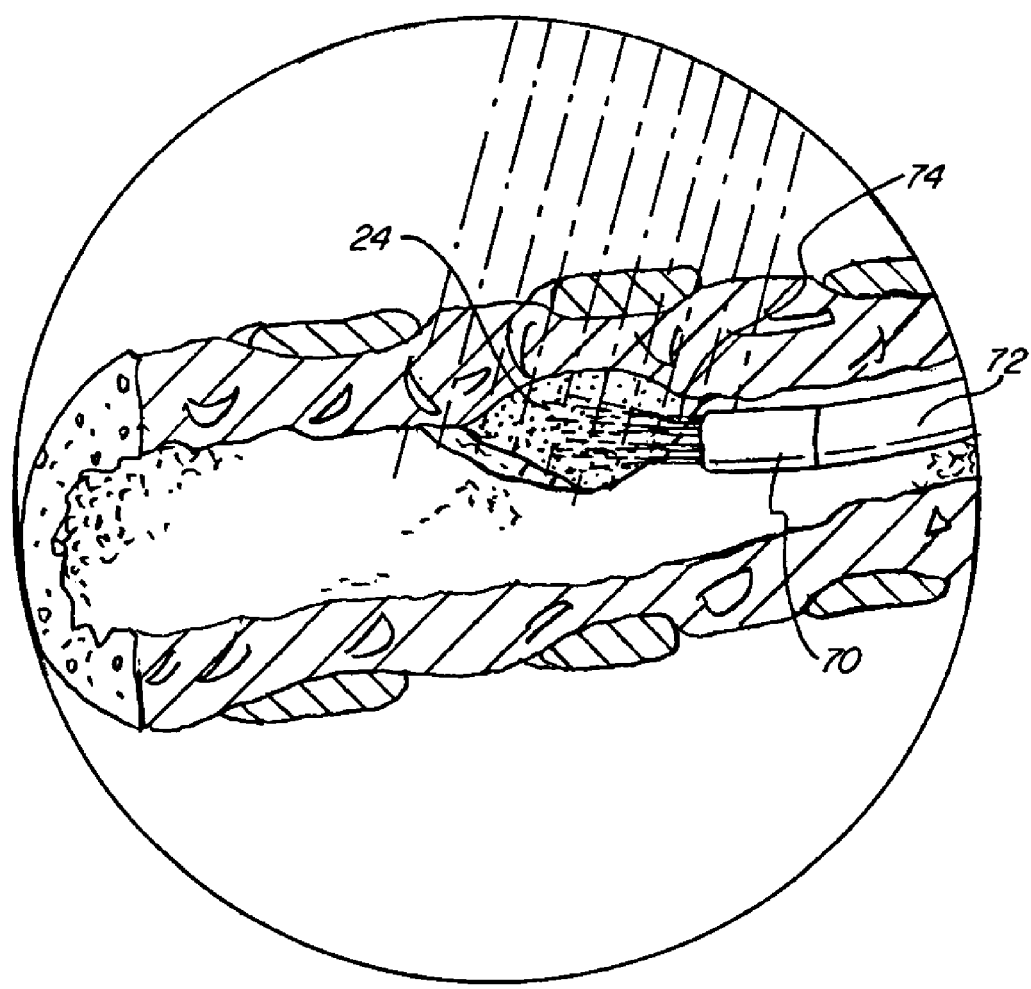
FIG. 4 is an enlarged view of a delivery device of the system of FIG. 1, positioned in a bodily lumen.

In another advantageous embodiment shown in FIG. 4, the delivery device is a delivery probe (70), such as that disclosed in U.S. Patent Publication No. 2011-0270184 by Gunday et al., the specification of which is hereby incorporated by reference herein in its entirety. By using a device such as this, the agent can be directly injected into the tumor tissue. The delivery probe (70) may be introduced into the patient's body via guide wires, catheters, and/or any other suitable medical devices. In one possible embodiment shown in FIG. 4, the delivery probe is positioned at a distal end of a catheter (72). Preferably, the insertion and positioning of the delivery probe (70) in a bodily cavity is performed with the assistance of an imaging device, such as described above. Once the delivery probe (70) is positioned at a target tumor tissue site (24), the oxygenating and/or photosensitizing agent is delivered to tissue via a delivery device (74), such as a plurality of needles.

Figure 5A:
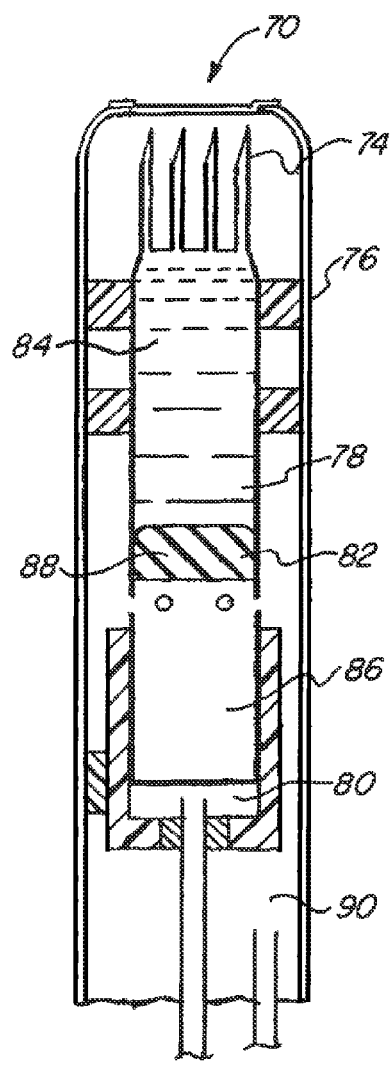
FIGS. 5A and 5B are cross-sectional views of the delivery device of FIG. 4, showing the delivery device in inactivated and activated positions.
Figure 5B:
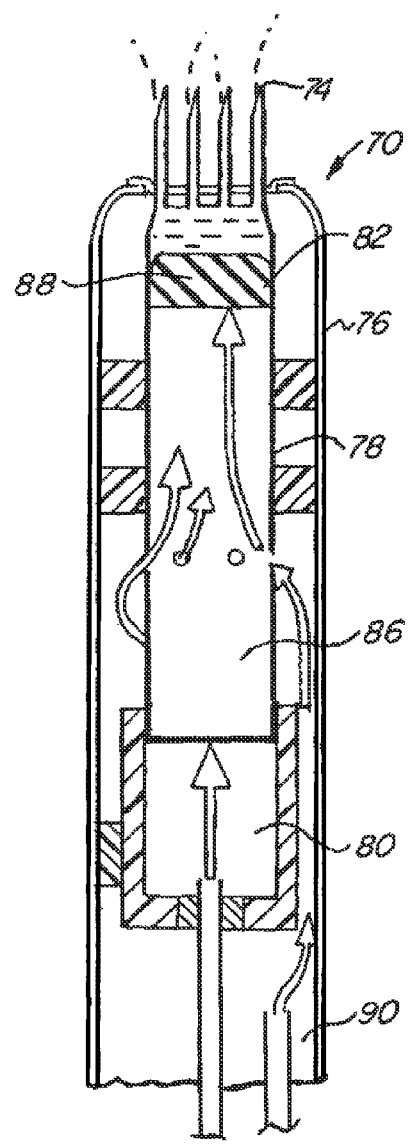

A detailed structure of the delivery probe (70) is illustrated in FIGS. 5A and 5B. The delivery probe (70) includes a housing (76) and at least one delivery capsule (78) for accommodating the oxygenating and/or photosensitizing agent to be delivered, movably arranged in the housing (76). The probe (70) also includes an actuation mechanism (80) for moving the capsule between an inactivated position, as shown in FIG. 5A, and an activated position, as shown in FIG. 5B, by providing at least one of a fluid and a vacuum. The delivery probe further includes an injection device (74), such as a plurality of needles, in fluid communication with the delivery capsule (78), and a delivery mechanism (82) for forcing the oxygenating/photosensitizing agent out of the capsule (78) via the injection device (74).

The delivery capsule (78) includes a first chamber (84) in fluid communication with the needles (74) for containing the agent to be delivered. The delivery capsule (78) further includes a second chamber (86) fluidly isolated from the first chamber (84) by a piston (88) slidably disposed in the delivery capsule. The piston (88) seals the agent in the first chamber (84) and moves forward as the second chamber (86) behind it is filled with the pressurized fluid (e.g., air), which in turn causes the agent in the chamber (84) to move out through the needles (74) and into the targeted tissue.

The outer housing (76) includes a delivery chamber (90) surrounding the delivery capsule (78). The delivery chamber is in fluid communication with the second chamber (86) of the delivery capsule (78) such that the pressurized fluid used to actuate the piston (88) is supplied from the delivery chamber (90) to the second chamber (86).

The outer housing (76) further includes an actuation chamber (80) fluidly isolated from the capsule (78) and the delivery chamber (90). The pressurized fluid is supplied to the actuation chamber (80) and is used to push the delivery capsule (78) forward, causing the needles (74) to extend beyond the distal end of the outer housing (76) and to penetrate the targeted tissue. After the oxygenating/photosensitizing agent is delivered to tumor tissue, a vacuum (e.g. negative pressure) is applied to the actuation chamber (90) to cause the delivery capsule (78) to retract back into the probe housing (76).

Further details regarding the structure and operation of the delivery probe are disclosed in U.S. Patent Publication No. 2011-0270184 by Gunday et al.

Figure 6:
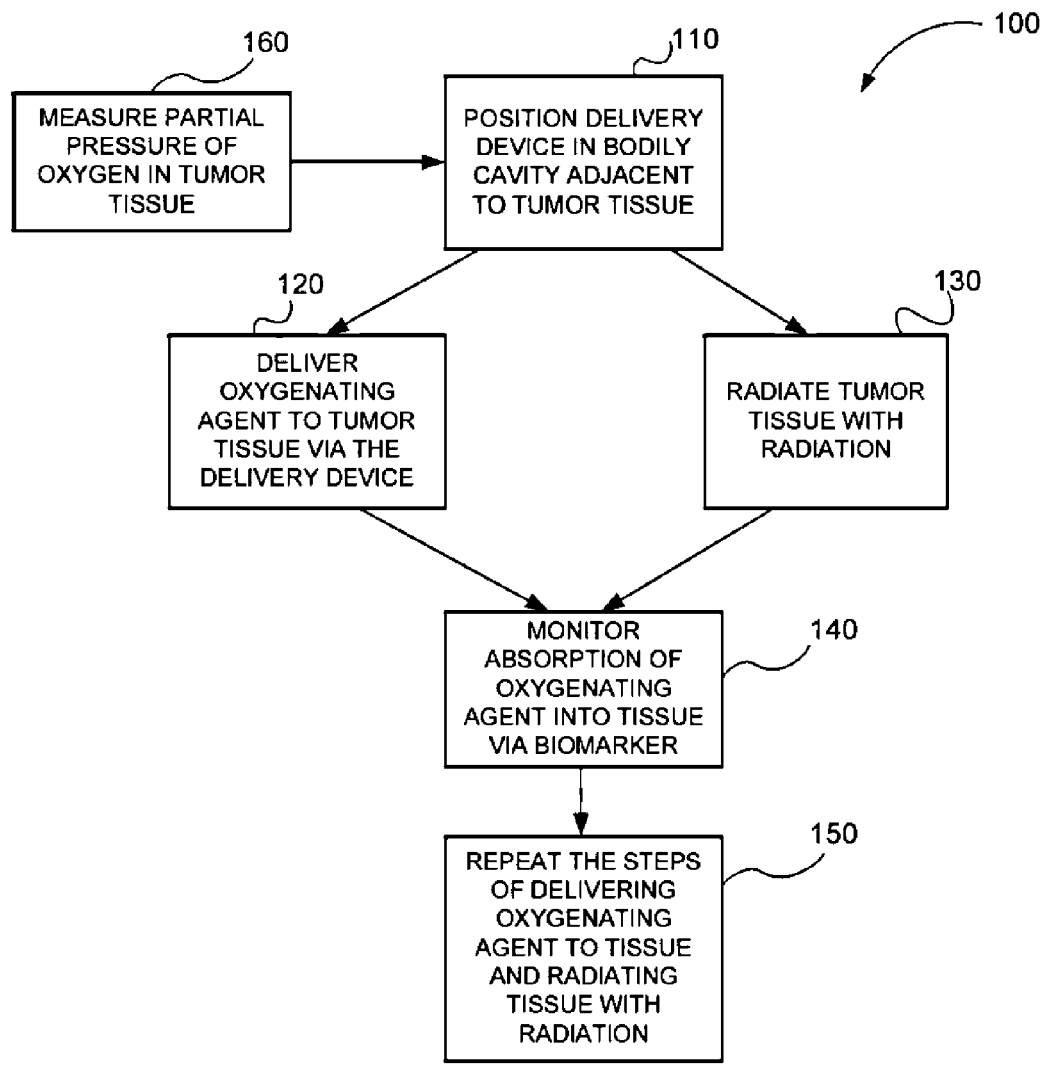
FIG. 6 is a flow diagram of a method for treatment of hypoxic tumors in accordance with the present invention.

FIG. 6 illustrates one possible embodiment of the method for treatment of hypoxic tumors in accordance with the present invention. The method (100) includes the step of positioning (110) a delivery device in a bodily cavity adjacent to tumor tissue. Any of the delivery devices described above can be utilized with the method of the present invention. Once the delivery device has reached the target tumor tissue site, an oxygenating agent is delivered (120) to the tissue via the delivery device and the tissue is radiated (130) by radiation. The radiation is delivered from any known radiation source commonly used for cancer radiation therapy.

In one possible embodiment shown in FIG. 1, the radiation source (22) is positioned outside of the patient's body, which is known as external beam radiotherapy. The radiation source (22) is pointed at a target tumor tissue site (24) and ionizing radiation beams (23) are directed at the tumor tissue (24) from outside the body.

In another possible embodiment, shown in FIG. 10B and further described below, the radiation source is local to the target area, such as in applications of intraoperative radiation therapy, such as, for example, intraoperative electron radiation therapy. This may be in the form of an internal probe (54) positioned adjacent the tumor tissue, which delivers a concentrated beam of electron radiation (56) to the target. The probe may be located at the end of a catheter (57), and may have a special tip (58) with walls for baffling the radiation, or particular optical elements for focusing the radiation on the tumor, so as not to damage the surrounding healthy tissue.

In another possible embodiment, radiation is delivered from sealed radioactive sources placed precisely in the target area (24), also known as brachytherapy. The radiation sources, such as small radioactive seeds or pellets, can be temporarily placed at the target tumor site for a set duration of time, e.g. several minutes or hours, before being withdrawn, or can be permanently implanted in the tumor site to gradually decay. In this embodiment, the same catheter that is used to deliver the oxygenating agent to the tumor site can be used to deliver the radioactive seeds, e.g. via an additional catheter lumen.

In yet another possible embodiment, the radiation source is a soluble form of radioactive substance, which is delivered to the target tissue site by injection or ingestion, commonly referred to as systemic radioisotope therapy. In the preferred embodiment, the soluble radioactive substance is delivered to tumor tissue (24) locally via the same delivery device (26) that is used to deliver oxygenating agent. For example, the balloon catheter system (40) illustrated in FIG. 2 can include two delivery lumens, one supplying the oxygenating agent and the other supplying a radioactive substance, such that these substances are delivered to the tumor tissue (24) separately, and if desired at different times and/or locations.

In the certain advantageous embodiments, the steps of delivering (120) the oxygenating agent and radiating (130) the tumor tissue with radiation are synchronized to achieve the most effective treatment. As described above, one of the most common problems encountered during the radiation therapy of cancerous tumors is that the tumor cells are deficient in oxygen, or hypoxic, which causes these cells to become resistant to radiation therapy. Thus, it is crucial during the radiation therapy to properly oxygenate the tumor tissue, which significantly increases the effectiveness of the therapy. The best results will typically be achieved when the oxygenation and the radiation of the tumor are synchronized such that these steps are performed substantially simultaneously, which is made possible by the system and method of the present invention.

In one embodiment, the oxygenating agent used in the method of the present invention comprises pure oxygen, such as medical grade oxygen, or oxygen bearing compounds, e.g. hydrogen peroxide, ozone, or hemoglobin-based oxygen carriers. In other possible embodiments, the oxygenating agent comprises an oxygenating therapeutic agent, such as doxorubicin or cisplatin.

In advantageous embodiments of the present invention, the oxygenating agent includes a biomarker such that the absorption of the oxygenating agent into the tumor tissue is monitored (140) via the biomarker. In some of these advantageous embodiments, CF3PM & MTFN-1 fluorinated radiopaque biomarkers are used. The biomarkers may be detected by various non-invasive imaging modalities, such as X-Ray, MRI, CT, ultrasound, spectroscopy, etc.

In additional embodiments, a contrast agent that allows or improves visualization via one or more imaging modalities can be used to image the absorption of the agent into the surrounding tumor tissues throughout the course of a procedure. Such agents may include, for example, radiocontrast agents, such as iodine or barium, to improve X-ray based imaging techniques; MRI contrast agents, such as gadolinium, to improve magnetic resonance imaging; and microbubble contrast agents, to improve ultrasound imaging.

Further, an appropriate inert dye or contrast media (e.g., radioactive, polarized, florescent, temperature sensitive) can also be added to the oxygenating agent such that the agent infusion rate and the amount of agent infused into the tumor tissue can be monitored, quantified, and recorded/displayed, such as, for example, by capturing and storing sequential video frames under different illumination conditions (UV, IR, polarized, color filters, etc.). Further, by deploying a contrast agent along with an oxygenating agent, one can visually identify the absorption depths and/or discern the requisite volumetric pressure, force, temperature, frequency and/or time to achieve efficacious delivery of the agent to the desired depth of penetration at the intended treatment site.

The steps of delivering the oxygenating agent and radiating the tumor tissue with radiation can be repeated (150) if needed to achieve the most effective radiation treatment.

In advantageous embodiments of the present invention, the method further includes the step of measuring (160) partial pressure of oxygen in the tumor tissue prior to delivering the oxygenating agent. In one advantageous embodiment, the partial pressure of oxygen in the tumor tissue is measured inside the bodily cavity via a probe inserted into the bodily cavity. The probe includes at least one sensor for measuring oxygen concentration of cancerous tissue. Any type of suitable sensor can be used in accordance with the present invention. The sensors are positioned in the proximity of the delivery device or any other suitable location along the probe.

Figure 7:
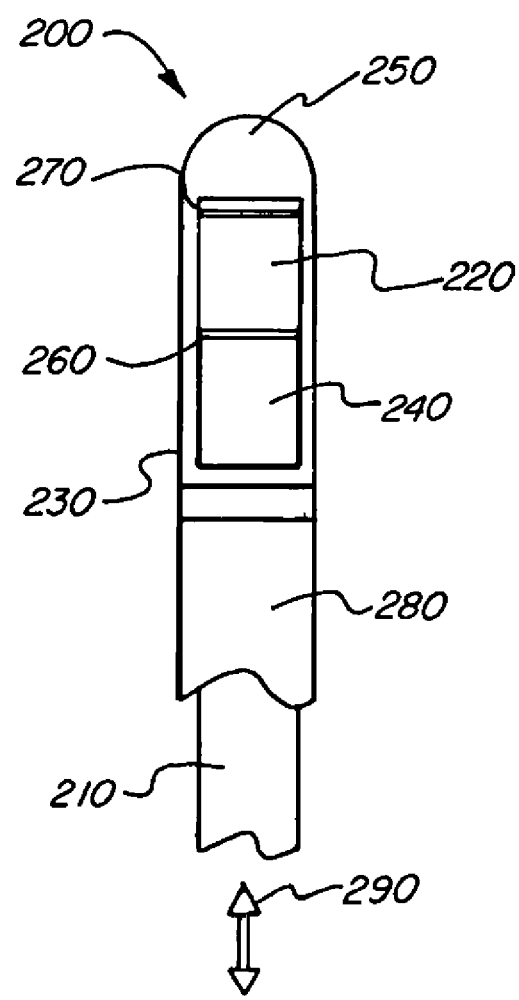
FIG. 7 is a schematic view of a forceps device used with the method of FIG. 6.

In another advantageous embodiment of the present invention, a partial oxygen pressure is measured outside of the patient's body. The tumor tissue is first extracted from the bodily cavity via any suitable device, such as the forceps device disclosed in U.S. Patent Publication No. 2011-0270126 by Gunday et al., the specification of which is hereby incorporated by reference herein in its entirety. The forceps device (200), shown in FIG. 7, includes a catheter (210) having a distal tip (230) with a rounded distal end (250). The distal tip includes a sampling chamber (220) which captures the tissue sample as it is being resected. The sampling chamber (220) remains closed during deployment of the forceps through a working channel of a guiding catheter or an endoscope until it reaches the target tissue.

The sampling chamber (220) has a movable cover (240). The distal end (260) of the cover (240) preferably has a sharpened edge to function as a cutting device for cutting the tissue sample. The opposing edge of the sampling chamber (220) can also be provided with a sharpened edge (270) to further assist in cutting off the tissue sample. The forceps (200) further include an actuation mechanism (280) for moving the movable cover (240) between a closed position and an opened position by providing at least one of a fluid and a vacuum. Once the forceps are inserted inside the patient's body and positioned adjacent to the target tumor tissue, the movable cover (220) is opened by applying at least one of a fluid and a vacuum (290), the tumor tissue sample is captured within the sampling chamber (220) by closing the movable cover (240), thereby cutting the sample off. Then, the forceps (200) are withdrawn from the bodily cavity, the captured tumor tissue sample is retrieved from the sample chamber (220) by opening the movable cover (240), and the sample is then analyzed for the oxygen content.

It is understood that the forceps embodiment discussed above is only an exemplary embodiment, and that any suitable device can be used to extract a sample of the tumor tissue in accordance with the present invention.

Figure 8:
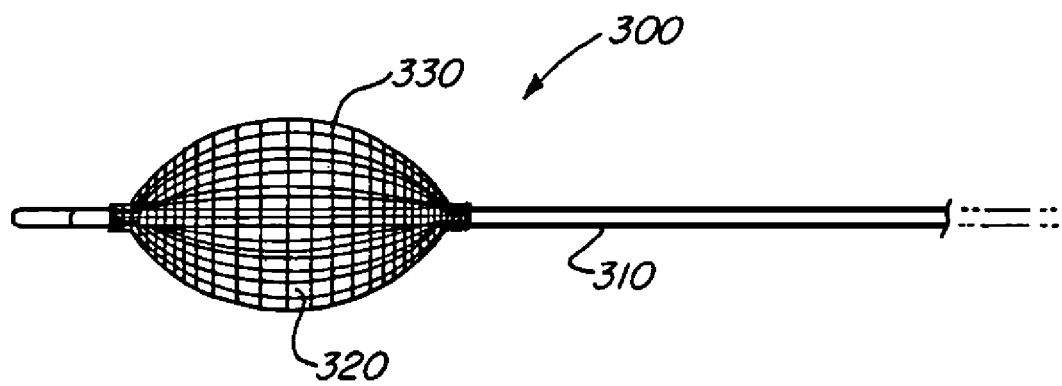
FIG. 8 is a schematic view of a resector balloon system used with the method of FIG. 6.

For example, in an additional embodiment, the step of measuring (160) partial pressure of oxygen comprises extracting at least a portion of the tumor tissue with a resector balloon system (300) described in U.S. Patent Publication No. 2010/0121270 by Gunday et al., the disclosure of which is incorporated by reference herein in its entirety. The resector balloon system (300), as shown in FIG. 8, includes a catheter (310) and at least one balloon (320) having an outer wall. The outer of the balloon has a resecting surface (330) for resecting the tumor tissue, which, in some embodiments, comprises a mesh. The catheter (310) is first inserted into a bodily cavity and positioned adjacent to the target tumor tissue site. Then, the balloon (320) is inflated via a fluid source, such as an electromagnetic pump, by supplying fluid thereto such that the resecting surface (330) of the balloon contacts the tumor tissue. In those cases, the balloon (320) is repeatedly deflated and inflated by supplying fluid thereto in pulsed fashion such that the repeated deflation and inflation causes the resecting surface (330) to resect the tumor tissue. Once the tissue is resected and extracted, a partial pressure of oxygen in the extracted tissue is determined by any suitable device outside of the bodily cavity.

Figure 9:
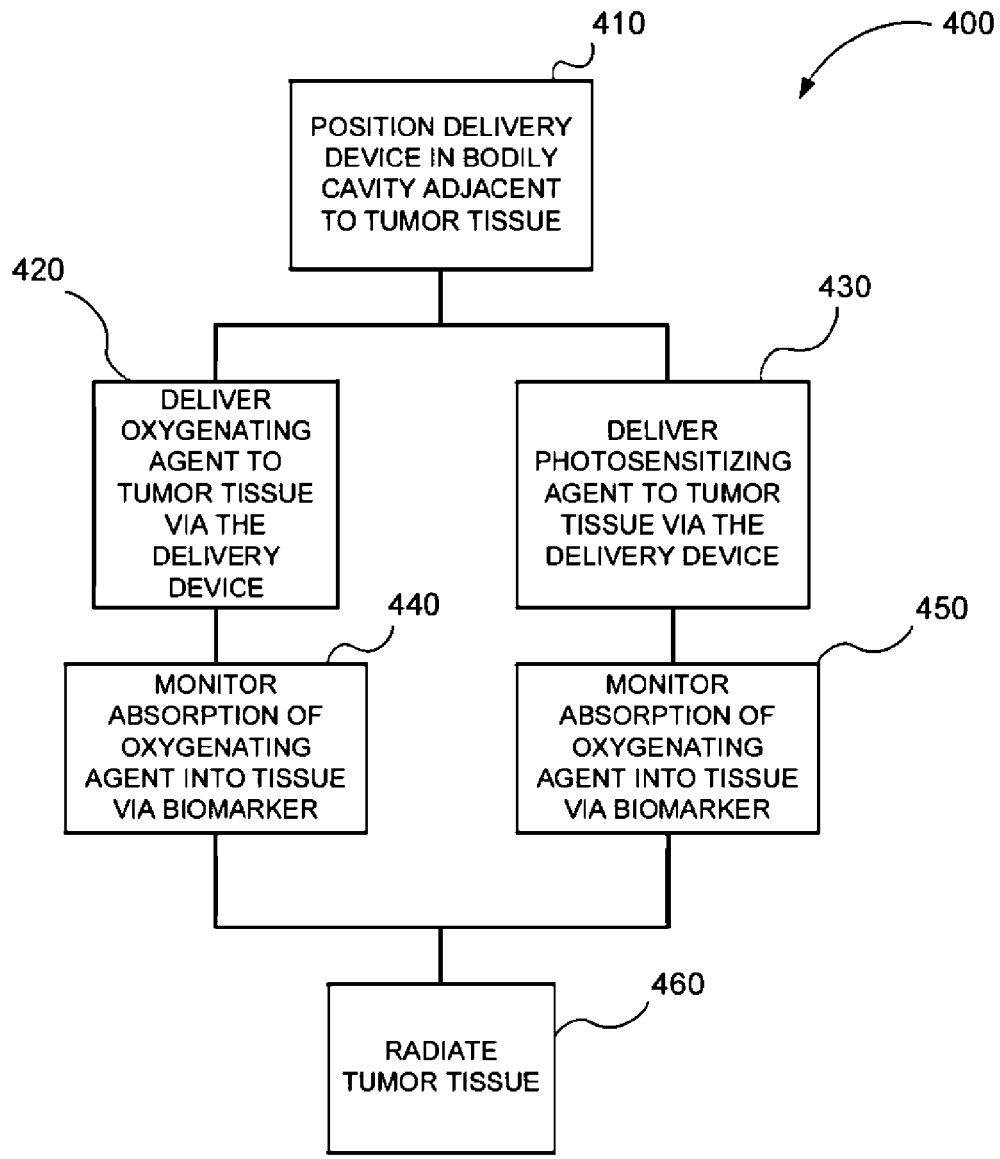
FIG. 9 is a flow diagram of a method for treatment of hypoxic tumors in accordance with the present invention.

In an advantageous embodiment, the method of the present invention further utilizes a photodynamic therapy, which involves the use of a photosensitizer, light, and tissue oxygen. In this embodiment, shown in FIG. 9, the method (400) includes the step of positioning (410) a delivery device in a bodily cavity adjacent to target tumor tissue, delivering (420) an oxygenating agent to tumor tissue via the delivery device, and delivering (430) a photosensitizing agent to tumor tissue via the delivery device. The oxygenating agent and photosensitizing agent can be delivered by any of the delivery devices described above. The agents can be delivered by a single delivery device having separate lumens, or can be delivered by two different delivery devices positioned adjacent to the target tissue. In some cases, it may be desirable to deliver the oxygenating and photosensitizing agents simultaneously, while in other cases, the agent may be delivered at different times. Further, the oxygenating and photosensitizing agents can be a part of the same therapeutic compound delivered via the delivery device. In certain advantageous embodiments, the method further includes the steps of monitoring (440, 450) delivery and absorption of the oxygenating agent and photosensitizing agent into surrounding tissue via a biomarker, such as described above.

A photosensitizing is a chemical compound that can be excited by light of a specific wavelength, typically visible or near-infrared light. Any known type of a photosensitizer may be used in accordance with the present invention, such as violanthrone, isoviolanthrone, fluoresceine, rubrene, 9,10-diphenylanthracene, tetracene, 13,13'-dibenzatronile, and levulinic acid. In certain advantageous embodiments, the photosensitizing agent is an up-converting phosphor.

Once the photosensitizing agent is delivered (420) to tumor tissue, the tissue is exposed (460) to light suitable for exciting the particular photosensitizing agent used. The light is delivered to tumor tissue via any suitable device, such as an endoscope or a fiber optic catheter. The photosensitizer is excited by light from a ground singlet state to an excited singlet state, and then undergoes further conversion to a longer-lived excited triplet state. When the photosensitizer and oxygenating agent are in proximity, an energy transfer takes place, which causes the photosensitizing agent to convert back to its ground singlet state. This, in turn, results in a creation of excited singlet state oxygen molecules, which are very aggressive chemical species that will very rapidly react with any nearby biomolecules, such as tumor cells, and ultimately kill tumor cells though apoptosis or necrosis.

In other advantageous embodiments on the present invention, the method includes the steps of delivering an oxygenating agent and a photosensitizing agent to tumor tissue, and then radiating the tissue with both ionizing radiation and light to achieve a more effective and potent anti-cancer treatment. It should also be noted that, in cases where the tumor tissue is not hypoxic, or where the delivery of an oxygenating agent is not necessary for some other reason, the photosensitizing agent alone can be delivered using any of the delivery devices described or referenced herein.

In some embodiments, the method further includes the delivery of a vaso-occlusive agents, nano-polymers or nano-particles in order to mitigate any ill effects of leaking tumor syndrome or capillary leak syndrome sometimes caused by the use of chemotherapeutic agents. These can be delivered locally, like the oxygenating agent, via one or more openings (52), as described above with respect to FIG. 2, or via a delivery probe (70), as shown described above with respect to FIGS. 4-5. The vaso-occlusive agents may also be introduced to the body from a location remote from the tumor, such as into the carotid artery, using a vascular catheter, and then into the pulmonary artery.

Figure 10A:
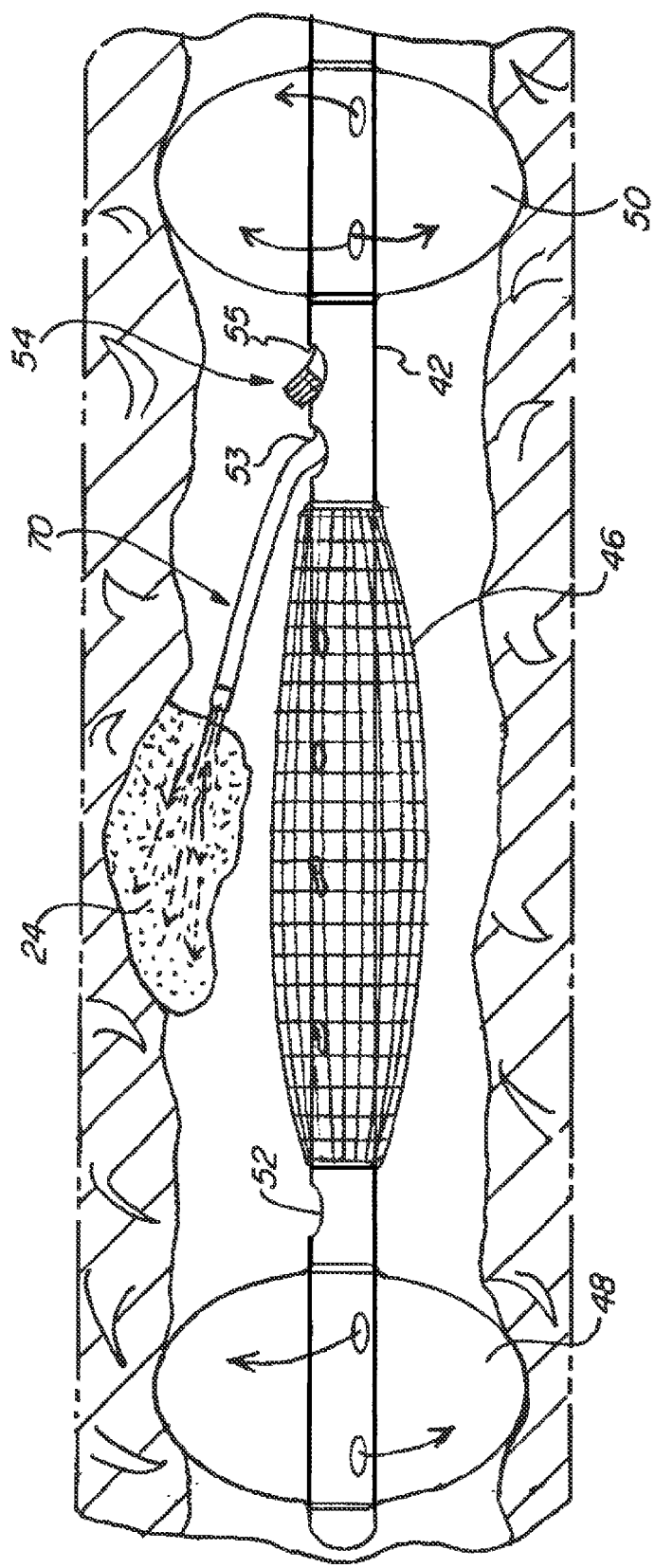
Figure 10C:
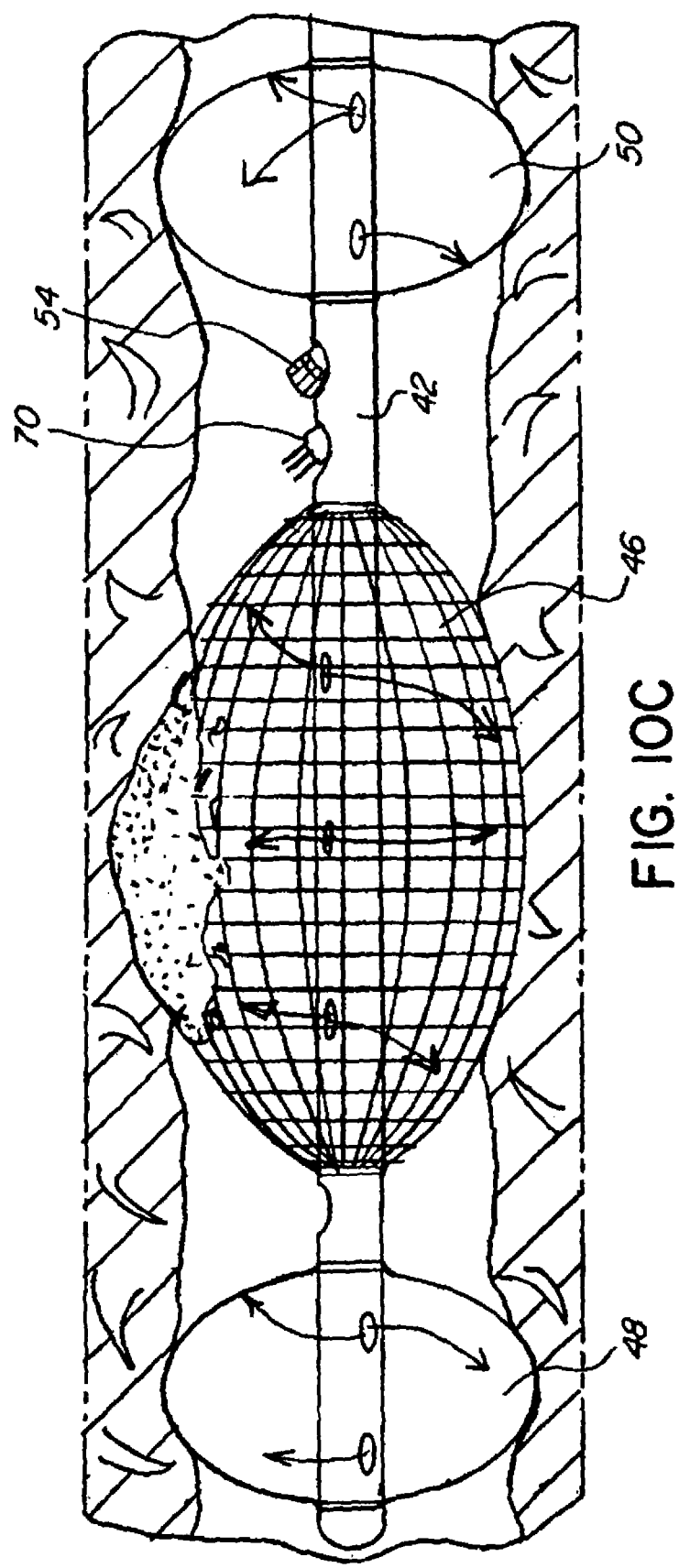

As shown in FIGS. 10A-C, in one embodiment, the invention includes the balloon catheter system (40), described above, which includes a catheter (42) with a first balloon (48), a second balloon (50) and a third balloon (46) positioned between the first and second balloons (48, 50). The catheter (42) has one or more lumens through which fluid is supplied to the balloons (46, 48, 50) via a fluid source to inflate the balloons, and at least one additional lumen for supplying an oxygenating agent, a photosensitizing agent, a vaso-occlusive agent, and/or a therapeutic/diagnostic agent (such as a chemotherapeutic drug) to tumor tissue (24), as well as imaging devices for viewing the same, via at least one opening (52, 53, 55) in the catheter (42). It is understood that any number or lumens and openings may be provided in the catheter (42) to deliver any number of things to assist insertion and positioning of the balloon catheter system (40) within the bodily cavity and to carry out various diagnostic or therapeutic procedures.

In a particular embodiment, as shown in FIG. 10A, the balloon catheter system (40) is inserted into a bodily cavity and, once in position, the outer balloons (48, 50) are inflated to anchor the catheter (42) in place and create a chamber for fluids therebetween. A delivery probe (70) is inserted into and moved through a first lumen and through an opening (53), where it is then be used to inject an oxygenating agent and/or photosensitizing into the tumor tissue (24). Prior to delivery, the agents may, for example, reside in a vessel in the previously described electro-pneumatic pump that is used to control balloon inflation. As shown in FIG. 10B, the internal probe (54) is then moved through another lumen of the catheter and out an opening (55), where it radiates the tumor tissue (24). Then, as shown in FIG. 10C, the balloon (46) is then inflated and deflated in pulsed fashion such that its resecting surface gradually resects the necrotic tumor tissue (24). These steps can be repeated multiple times in order to facilitate complete removal of the tumor tissue as necessary.

Additionally, a therapeutic and/or diagnostic agent may be supplied via an opening (52) in order to help attack the tumor tissue, heal surrounding tissue, or facilitate diagnostic analysis of the tissue removal. Likewise, a vaso-occlusive agent can be delivered via one or more openings in the catheter (42). Alternatively, the vaso-occlusive, therapeutic, or diagnostic agents can be injected into the desired tissue using a device such as the injection device (70) used to deliver the oxygenating agent/photosensitizing agent.

While multiple lumens and openings in the catheter (42) are described for delivering these various devices to the target site, it should be noted that a single lumen may also be employed by simply withdrawing one device and subsequently inserting another device into, or supplying an agent through, the same lumen.

It should be noted that while the above has been described with reference to tumors, the invention can also be applied to other tissues and pathologies. It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for treatment of hypoxic tumors comprising the steps of:
   positioning a catheter having at least one inflatable balloon positioned adjacent a distal end thereof in a bodily cavity adjacent to target tissue;
   delivering an oxygenating agent to the target tissue via at least one opening in said catheter;
   radiating the target tissue with radiation; and
   inflating said at least one inflatable balloon by supplying fluid thereto via said catheter such that a resecting outer surface of said balloon contacts the radiated target tissue and resects said tissue.

2. The method of claim 1, wherein the steps of delivering the oxygenating agent to the target tissue and radiating the target tissue with radiation are synchronized.

3. The method of claim 1, wherein the oxygenating agent comprises oxygen.

4. The method of claim 1, wherein the oxygenating agent comprises an oxygenating therapeutic agent.

5. The method of claim 4, wherein the oxygenating therapeutic agent comprises doxorubicin.

6. The method of claim 1, wherein the radiation comprises ionizing radiation.

7. The method of claim 6, wherein the radiation comprises light, and the method further comprises the step of delivering a photosensitizing agent to the target tissue via the at least one opening in said catheter.

8. The method of claim 7, wherein the photosensitizing agent is an up-converting phosphor.

9. The method of claim 1, wherein the radiation comprises light and ionizing radiation, and wherein the oxygenating agent comprises a photosensitizing agent.

10. The method of claim 1, wherein the oxygenating agent comprises a biomarker, and the method further comprises the step of monitoring absorption of the oxygenating agent into the tumor tissue via the biomarker.

11. The method of claim 10, wherein the biomarker is a radiopaque marker.

12. The method of claim 10, wherein the biomarker is a fluorinated compound.

13. The method of claim 1, wherein said catheter has a first lumen through which fluid is supplied to said at least one balloon to inflate the balloon and a second lumen for supplying the oxygenating agent to the target tissue via said at least one opening in the catheter.

14. The method of claim 1, wherein the step of delivering an oxygenating agent to the target tissue comprises injecting the oxygenating agent into the target tissue.

15. The method of claim 1, further comprising the step of measuring partial pressure of oxygen in the target tissue prior to delivering the oxygenating agent.

16. The method of claim 15, wherein the step of measuring partial pressure of oxygen comprises determining partial pressure of oxygen in the bodily cavity via a probe inserted into the bodily cavity.

17. The method of claim 1, wherein the step of radiating the target tissue with radiation comprises radiating the target tissue from an external source positioned outside of a patient's body.

18. The method of claim 1, wherein the step of radiating the target tissue with radiation comprises radiating the target tissue locally by positioning a source of radiation in the bodily cavity adjacent to the target tissue.

19. The method of claim 18, wherein the source of radiation positioned in the bodily cavity comprises a probe for radiating the target tissue.

20. The method of claim 19, wherein the probe delivers a beam of electron radiation to the target tissue.

21. The method of claim 1, further comprising the step of delivering a vaso-occlusive agent to the target tissue.

22. The method of claim 21, wherein the vaso-occlusive agent comprises an antifibrinolytic drug eluting nanoparticle.

23. The method claim 22, wherein the nanoparticle comprises a tranexamic acid eluting PLGA microsphere.

24. The method of claim 1, further comprising the steps of repeating the steps of radiating the target tissue and resecting the target tissue.

25. The method of claim 1, wherein the resecting outer surface comprises a mesh disposed on an outer wall of said at least one balloon.

26. A method for treatment of hypoxic tumors comprising the steps of:
   positioning a delivery device in a bodily cavity adjacent to tumor tissue;
   measuring partial pressure of oxygen in the tumor tissue;
   delivering an oxygenating agent to the tumor tissue via said delivery device; and
   radiating the tumor tissue with radiation;
   wherein the step of measuring partial pressure of oxygen comprises extracting at least a portion of the tumor tissue with forceps and determining partial pressure of oxygen in the extracted tissue outside of the bodily cavity.

27. The method of claim 26, wherein the forceps comprise:
   a catheter;
   a sampling chamber positioned at a distal end of the catheter and having a movable cover; and
   an actuation mechanism for moving the movable cover between a closed position and an opened position by providing at least one of a fluid and a vacuum.

28. A method for treatment of hypoxic tumors comprising the steps of:
   positioning a delivery device in a bodily cavity adjacent to tumor tissue;
   measuring partial pressure of oxygen in the tumor tissue;
   delivering an oxygenating agent to the tumor tissue via said delivery device; and
   radiating the tumor tissue with radiation;
   wherein the step of measuring partial pressure of oxygen comprises extracting at least a portion of the tumor tissue with a resector balloon system and determining partial pressure of oxygen in the extracted tissue outside of the bodily cavity.

29. The method of claim 28, wherein the resector balloon system comprises a catheter and at least one balloon having an outer wall, said outer wall comprising a resecting surface for resecting the tumor tissue.

* * * * *